(12) United States Patent
Windridge et al.

(10) Patent No.: US 10,984,351 B2
(45) Date of Patent: Apr. 20, 2021

(54) SYSTEM FOR REMINDING A USER

(71) Applicant: KONINKLIJKE PHILIPS N.V., Eindhoven (NL)

(72) Inventors: Melanie Jane Windridge, Amersham (GB); Julian Charles Nolan, Pully (CH); Cees Van Berkel, Hove (GB); Joyca Petra Wilma Lacroix, Eindhoven (NL); Jan Tatousek, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1119 days.

(21) Appl. No.: 15/025,568

(22) PCT Filed: Sep. 28, 2014

(86) PCT No.: PCT/EP2014/070713
§ 371 (c)(1),
(2) Date: Mar. 29, 2016

(87) PCT Pub. No.: WO2015/055404
PCT Pub. Date: Apr. 23, 2015

(65) Prior Publication Data
US 2016/0232327 A1 Aug. 11, 2016

(30) Foreign Application Priority Data

Oct. 15, 2013 (EP) ..................................... 13188692

(51) Int. Cl.
*G06Q 10/06* (2012.01)
*G16H 20/00* (2018.01)
(Continued)

(52) U.S. Cl.
CPC ......... *G06Q 10/06* (2013.01); *G06Q 10/1097* (2013.01); *G08B 21/24* (2013.01); *G16H 20/00* (2018.01)

(58) Field of Classification Search
CPC ............... G06F 19/3481; G06F 19/328; G06F 19/3418; G06F 19/3456; G06F 19/3462;
(Continued)

(56) References Cited

U.S. PATENT DOCUMENTS

2007/0021979 A1* 1/2007 Cosentino ............. G16H 10/65
705/2
2011/0016056 A1* 1/2011 Hargroder ............. G06Q 40/08
705/325

(Continued)

FOREIGN PATENT DOCUMENTS

EP 2485704 A1 8/2012
TW 201209750 A 3/2012
(Continued)

OTHER PUBLICATIONS

Lei et al, "MHS: A Multimedia System for Improving Medication Adherence in Elderly Care", IEEE Systmes Journal, vol. 5 No. 4, 2011, pp. 506-517.
(Continued)

*Primary Examiner* — Fonya M Long
*Assistant Examiner* — Anthony Michael Balaj

(57) ABSTRACT

A system for providing a reminder to a user is provided that stores reminder information relating to a task that the user wishes to be reminded about, along with activity information comprising information on activities that are considered to have an effect on the efficacy of the reminder associated with the task. The system monitors the user to determine if the activities in the activity information are being performed to produce a monitoring result, and then determines when to
(Continued)

remind the user about the task based on the monitoring result by comparing the monitoring result to a threshold. A reminder alert is then output to the user when the monitoring result meets or exceeds the threshold.

14 Claims, 5 Drawing Sheets

(51) Int. Cl.
*G06Q 10/10* (2012.01)
*G08B 21/24* (2006.01)

(58) Field of Classification Search
CPC .... G06Q 10/06; G06Q 10/1097; G06Q 50/20; G06Q 21/24
See application file for complete search history.

(56) References Cited

U.S. PATENT DOCUMENTS

| | | | |
|---|---|---|---|
| 2011/0225004 A1 | 9/2011 | Loncar | |
| 2011/0298614 A1* | 12/2011 | Bells | G06Q 10/109 |
| | | | 340/539.13 |
| 2012/0154120 A1 | 6/2012 | Cohen et al. | |
| 2012/0160716 A1 | 6/2012 | Chan et al. | |
| 2012/0166216 A1 | 6/2012 | Lim et al. | |
| 2012/0173319 A1 | 7/2012 | Ferrara | |
| 2013/0004923 A1* | 1/2013 | Utter, II | A61B 5/0022 |
| | | | 434/127 |
| 2013/0216989 A1* | 8/2013 | Cuthbert | A61B 5/721 |
| | | | 434/238 |
| 2013/0325404 A1* | 12/2013 | Yuen | A61B 5/1118 |
| | | | 702/182 |
| 2014/0257851 A1* | 9/2014 | Walker | G06Q 30/0269 |
| | | | 705/3 |

FOREIGN PATENT DOCUMENTS

| | | |
|---|---|---|
| WO | 2011042840 A1 | 4/2011 |
| WO | 2012050882 A1 | 4/2012 |

OTHER PUBLICATIONS

Sengul et al, "A Statistical Reasoning System for Medication Prompting", Ubiquitous Compouting, 2007, pp. 1-18.

* cited by examiner

SYSTEM FOR REMINDING A USER

CROSS-REFERENCE TO PRIOR APPLICATIONS

This application is the U.S. National Phase application under 35 U.S.C. § 371 of International Application No. PCT/EP2014/070713, filed on Sep. 28, 2014, which claims the benefit of European Patent Application No. 13188692.1, filed on Oct. 15, 2013. These applications are hereby incorporated by reference herein.

FIELD OF THE INVENTION

The present invention relates to a system and method for reminding a user about an activity.

BACKGROUND OF THE INVENTION

There are many reasons why users may wish to be reminded about activities. Ways of alerting reminding users of activities have existed for a long time. These range from old-fashioned alarms to web-based or mobile device applications. Taking a mobile device application as an example, a user will typically set a task (e.g. buy more milk) and a time to be reminded (e.g. tomorrow at 8:00 am). The mobile device application will then issue the reminder (e.g. using an audible alert with an onscreen notification) at the preset/predefined time.

There are many situations where the reminder is very important. For example, a patient with a long term health condition may have a therapeutic regime prescribed by a doctor, that the patient should then adhere to at set time periods or within certain time boundaries. The therapeutic regime may manage the patient's symptoms, with the objective of the therapeutic regime being to manage the patient's condition and to help to achieve a positive therapy outcome. It will be appreciated that non-adherence with the therapeutic regime may cause the patient's health to deteriorate.

For many long term health conditions, the therapeutic regime requires medication to be taken regularly (e.g. one dose, three times a day). If the medication is not taken regularly or in the correct amounts (i.e. if the therapeutic regime is not adhered to), then this may impact the clinical outcome. It is known to use conventional reminder system approaches (e.g. mobile device applications) to attempt to encourage users to adhere to their therapeutic regime (e.g. by taking their medication on time). However, such conventional systems provide reminders at particular, preset times of the day depending on the medication schedule.

It is also known to provide dedicated devices for medication management. These are generally dispensers that can be programmed to issue alerts and release medication at pre-defined times. They often include a means of monitoring compliance by way of detecting if the medication has been removed from the dispenser. As an example of such devices, EP2485704 discloses a medication dispenser that provides a reminder in the form of light and sound emitted by the dispenser itself. The dispenser can connect to a remote server to exchange information on the dispensing and the patient's adherence.

All the conventional systems mentioned above provide reminders at preset times of the day depending on how they are configured. This approach is, however, inflexible. As a consequence, it allows for providing reminders at moments that the receiver is less likely to be receptive and responsive to these reminders due to being engaged in other activities that decrease the efficacy of the reminder.

SUMMARY OF THE INVENTION

It is an object of the invention to provide a system for reminding a user which substantially alleviates or overcomes the problems mentioned above of providing reminders at moments that the receiver is less likely to be receptive and responsive to the reminder. In particular, it is an object of the invention to provide a system for monitoring a user that provides a flexible approach that overcomes the technical shortcomings of known reminder systems.

According to an aspect of the present invention, there is provided a system for providing a reminder to a user, the system comprising: a reminder datastore arranged to store reminder information relating to a task that the user wishes to be reminded about; an activity datastore arranged to store activity information comprising information on activities that are considered to have an effect on the efficacy of the reminder associated with the task; a monitor mechanism arranged to monitor the user to determine if the user is performing one or more activities for which activity information is stored in the activity datastore and to produce a monitoring result based on the determination; a reminder processor arranged to determine when to remind the user about the task based on the monitoring result, wherein the reminder processor is arranged to compare the monitoring result to a stored parameter; an output mechanism arranged to output a reminder alert to the user on the basis of the comparison of the monitoring result and the stored parameter.

In some embodiments, the stored parameter is a threshold, and the output mechanism is arranged to output the reminder alert to the user when the monitoring result meets or exceeds the threshold.

It is known that people are more likely to do something that they are reminded about a task when they are not distracted or doing something else. The proposed invention is a system that generates an alert when a user is most likely to be receptive to carrying out the task.

This arrangement provides the advantage that reminders are provided at the most opportune time for the task, based on the activities of the user at the time of the reminder. In some embodiments, this is done by delivering the reminder when the user is carryout out (or not carrying out) certain activities that are considered to have a positive or negative effect on the efficacy of the reminder. This enables embodiments of the invention to provide greatly improved reminders when compared to conventional systems that simply provide reminders at an absolute preset time. The reminder system according to this embodiment can be used to ensure that the reminder is delivered when the user is likely to be receptive to the reminder.

In some embodiments, the stored parameter is a threshold, and the output mechanism is arranged to output the reminder alert to the user when the monitoring result meets or exceeds the threshold.

In some embodiments, the monitor mechanism is arranged to monitor each activity in the activity information, and to assign an activity score based on whether that activity is being performed. By doing this, the monitor mechanism can determine the monitor result based on the activity scores. In some embodiments, the monitoring result is the sum of the activity scores. In other embodiments, the monitoring result can be calculated based on the activity scores in a different way.

In some embodiments, the monitor mechanism is arranged to assign different weight values to different activities scores. Hence, the relative importance of different activity scores on the efficacy of the reminder can be taken into account when calculating the monitoring result.

In some embodiments, the reminder processor is arranged to determine if the task is performed following the output of the alert, and to use the activities scores to determine a compliance result. Hence, whether the reminder has been acted on can be monitored, and this information can be used to tailor various aspects of the system. In some embodiments, the system is arranged to use the compliance result to adjust the threshold. In some embodiments, the system is arranged to use the compliance result to adjust the weight values of the activity scores.

Using a compliance result in these ways is useful in many circumstances. For example, even though embodiments of the invention provide reminders that are more likely to be acted upon than conventional reminder systems, it is still possible that the reminder will be ignored. By using the compliance result in this way, the system of such embodiments can adapt to the precise demands of the user in order to improve the efficiency of the reminder system.

In some embodiments, the reminder information includes information concerning a time window associated with the task, and the output mechanism is arranged to only output reminders within the time window. Hence, the system will only remind the user about the task, at the appropriate time within the time window for that task.

In some embodiments, the reminder information relates to a task that is periodically repeated, and the time window can be determined on the basis of when the task was last performed.

In some embodiments, the threshold is arranged to vary with time, and the threshold is arranged to be lowered with increasing time within the time window.

In some embodiments, the output mechanism is arranged to output a reminder alert to the user at the end of the time window, regardless of the monitoring result.

In some embodiments, the reminder information includes information concerning a missed reminder cost, the missed reminder cost relating to a consequence of the reminder not being performed in the time window. In such embodiments, the missed reminder relates to the consequences of not acting on the reminder. For example, some tasks might be crucial and need to be performed within their time window (e.g. taking a dose of medication). In such embodiments, the missed reminder cost may be a variable that increases as the time window for the reminder nears closing.

In some embodiments, the output mechanism to determine the nature of the reminder alert to the user based on the missed reminder cost. In some embodiments, the system is arranged to adjust the threshold based on the missed reminder cost. In some embodiments, the system is arranged to adjust the weight values of the activity scores based on the missed reminder cost.

In some embodiments, the task relates to an aspect of the user's therapeutic regime. There are many situations where the reminder is very important. For example, a patient with a long term health condition may have a therapeutic regime prescribed by a doctor, that the patient should then adhere to at set time periods. The therapeutic regime may manage the patient's symptoms, with the objective of the therapeutic regime being to manage the patient's condition and to help to achieve a positive therapy outcome. It will be appreciated that non-adherence with the therapeutic regime may cause the patient's health to deteriorate.

The activities for which activity information is stored in the activity information can include actions of the user or a passive activities such as where the user is located. The activity could relate to any activity that the user may be engaged in or any state of the user. The activity could relate to an action of the user (e.g. watching television) or a passive activity (e.g. being at a certain location or being with a certain individual).

In some embodiments, the system further comprises a user preference datastore arranged to store information on one or more reminder preferences of the user, wherein the reminder processor arranged to determine when to remind the user about the task taking into account the or each reminder preference of the user. For example, the threshold could be lowered or raised based on certain times of the day that the user has indicated have either a negative or positivity effect on the efficacy of the reminder associated with the task. By measuring activities of the user, it is possible to gauge information on the user's likely emotional or cognitive state. For example, if the user's sleep is measured, and it is found that that user's sleep activity is lower than normal (or lower than a set level), then the system could determine that the user may be tired, and hence output (or not output) reminders appropriately.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
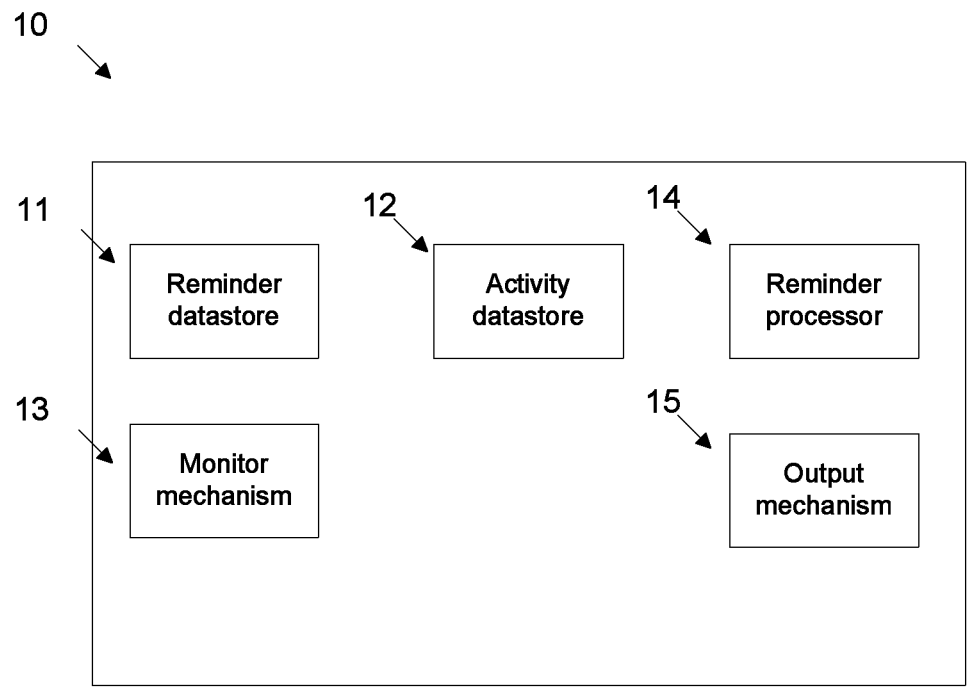
FIG. 1 schematically shows a system for reminding a user according to a first embodiment of the invention.

FIG. 1 schematically shows a system 10 for reminding a user according to a first embodiment of the invention.

The system 10 comprises a reminder datastore 11, an activity datastore 12, a monitor mechanism 13, a reminder processor 14, and an output mechanism 15.

The reminder datastore 11 is arranged to store reminder information about reminders relevant to the user. For example, the reminder datastore 11 could store information that the user would like to be reminded about a certain task on a certain day, for example to pay a utility bill on the 17$^{th}$ of the month. In embodiments of the invention, the reminders can relate to any task that the user might want to be reminded about.

The activity datastore 12 is arranged to store activity information regarding activities that could be carried out by the user. As described in more detail below, the activity information is used by the monitor mechanism 13 to monitor the user, so as to enable reminders to be delivered at an optimum time, e.g. by delivering the reminder when the user is carryout out (or not carrying out) certain activities. The activity information can be set by the user or by a third party.

The term "activity" is used herein in the broad sense, to encompass any activity that the user may be engaged in or any state of the user. The activity could relate to an action of the user (e.g. watching television) or a passive activity (e.g. being at a certain location).

The monitor mechanism 13 is arranged to monitor the user using the activity information to provide a monitoring result. In other words, the monitor mechanism 13 is arranged to monitor the user based on the activities stored in the activity information.

The reminder processor 14 is arranged to determine when to remind the user about the task based on the monitoring result. The reminder processor 14 is arranged to compare the monitoring result against a threshold.

The output mechanism 15 is arranged to output an alert to the user as a reminder if the monitoring result is above the threshold. In this embodiment, the output mechanism 15 is arranged to output an audible and visual alert to the user. Hence, in this embodiment, the output mechanism 15 comprises a speaker and a display. Other embodiments can use other ways of providing a reminder alert to the user.

In this embodiment, the reminder datastore 11, the activity datastore 12, the monitor mechanism 13, the reminder processor 14, and the output mechanism 15 are provided on the same apparatus, i.e. the same device. For example, such an apparatus could be a smart phone, tablet, general purpose computer or other suitable apparatus. In other embodiments, the apparatus may communicate with external additional monitor mechanisms. Also, in other embodiments, the elements of the system could be provided on different devices.

In some embodiments, the monitor mechanism 13 can have local components distributed across several devices. Those could either communicate with a local control unit (represented by one of the monitoring devices or by a separate device) or with a remote system or both of these approaches can be combined in one system. In some embodiments, the monitor mechanism 13 can have a form of a remote system (e.g. web server) accessed by the user using a local terminal (e.g. computer, smart phone, tablet etc.).

Furthermore, in some embodiments, the output mechanism 15 can have local components distributed across several devices. For example, one component could display a visual alert, while another component could play an audible component.

In some embodiments, the monitor mechanism 13 can be in the same device as the output mechanism 15 or in separate devices (e.g. one device monitors the user and another device displays the reminder alerts).

Figure 2:
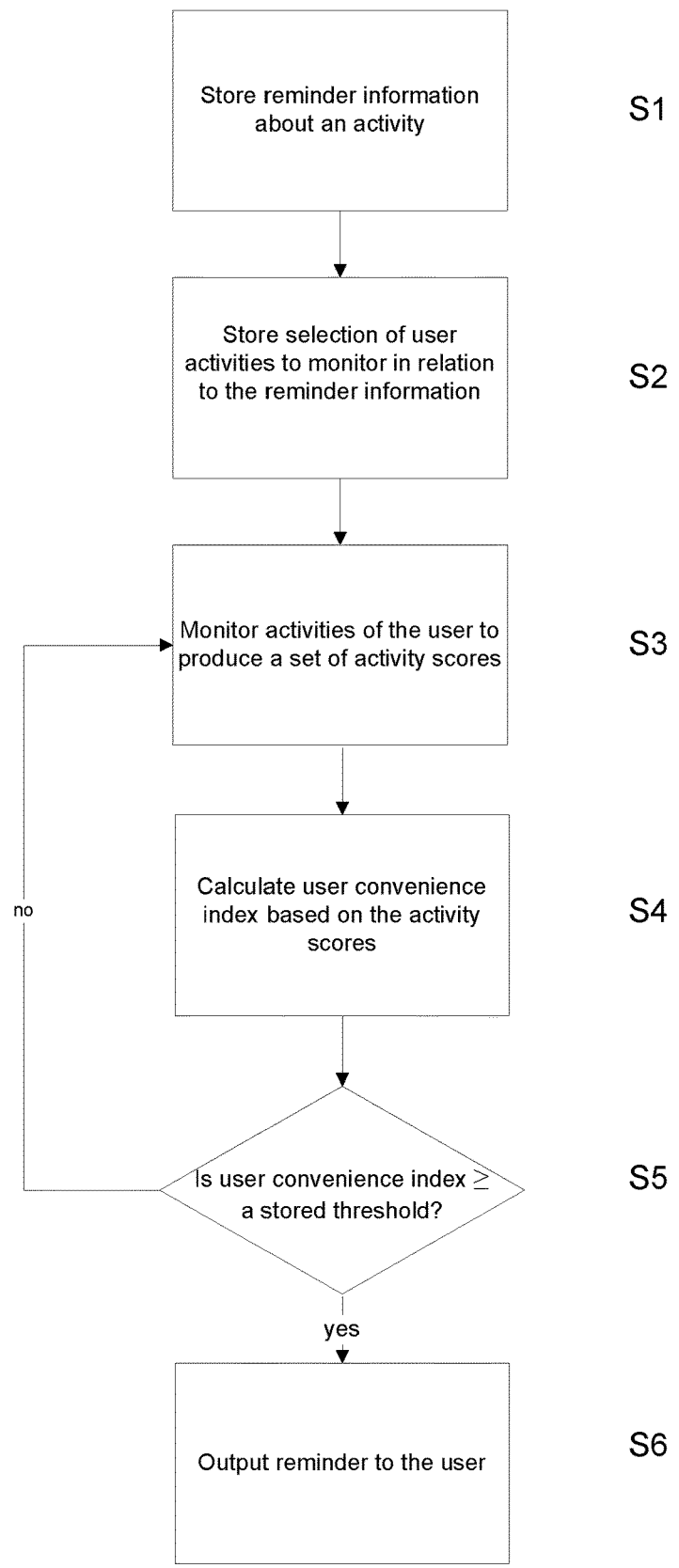
FIG. 2 shows a flow diagram explaining the operation of the system of the first embodiment.

FIG. 2 shows a flow diagram explaining the operation of the system 10.

At step S1 of FIG. 2, the system 10 stores reminder information about a task that the user wishes to be reminded about in the reminder database 11. In this embodiment, the system 10 determines the reminder information using a user input. In other words, the user enters a task that they would like to be reminded about using a suitable input means in the system 10.

At step S2, the system 10 stores a selection of user activities to monitor the user as activity information in the activity datastore 12. The activity information comprises a selection of activities that could be carried out by the user that are considered likely to have an effect on the efficacy of the reminder in the reminder information. For example, if the task associated with the reminder information (e.g. pay a utility bill) is associated with using the internet, then the efficacy of the reminder associated with that task may be increased if the reminder alert is delivered when the user is using the internet. In contrast, the efficacy of the reminder associated with that task may be decreased if the reminder alert is delivered when the user is doing a non-interruptible task such as making a telephone call.

In this embodiment, the system 10 determines the activity information using a user input. In other words, the user enters a set of activities that are relevant to the efficacy of the reminder associated with the task, along with an indication whether the activity is considered to be likely to have a positive or negative effect on the efficacy of the reminder.

At step S3, the monitor mechanism 13 of system 10 monitors the user using the activity information. In other words, the monitor mechanism 13 monitors whether the user is carrying out the activities included in the activity information. In this embodiment, the monitor mechanism 13 determines if each activity in the activity information is being carried out, and then assigns a set of activity scores.

A step S4, the monitor mechanism 13 calculates a user convenience index using the activity scores. In this embodiment, the user convenience index is a monitoring result that is a sum of the activity scores. In other embodiments, the monitor mechanism 13 can determine the monitoring result in other ways.

Then, at step S5, the reminder processor 14 calculates whether the user convenience index is greater than or equal to a threshold. If the user convenience index is greater than or equal to the threshold, then, at step S6, the output mechanism 15 outputs an alert to the user about the task as a reminder. If the user convenience index is not above the threshold, then the monitoring of the activities the user using the activity information continues (step S3).

In this embodiment, the reminder alert takes the form of an audible and visual alert on the device of the system 10. In other embodiments, the reminder may be communicated in any of a variety of ways including audible, visual or tactile signals to a smart phone, nearby display, and the user of a wearable device.

To help explain steps S3, S4 and S5, an example reminder scenario will be discussed. In this example, the user wishes to be reminded about paying a credit card bill by their smart phone, with the smart phone acting as the device of the system 10 in this embodiment. This may be because the user wishes to review the credit card bill before payment, thus making such a bill unsuitable for automatic payment. Hence, the user enters the reminder on their smart home, which is then stored in the reminder datastore 11 (at step S1 of FIG. 2). The reminder datastore 11 would be part of the memory or other storage unit of the smart phone.

In this example, the user could input the reminder using a suitable user interface on the smart phone (e.g. a suitable application), entering the text "Pay Credit Card Bill". In this example, the reminder is not associated with a time period for carrying out the task.

In this example, the user is then presented with a list of activities by the smart phone that that can be monitored and that are relevant to the efficacy of reminders. The user can then select those activities from the list, and indicate whether those activities are likely to have a positive or negative impact on the efficacy of the reminder. In other embodiments, the system can determine which activities are likely to have a positive or negative impact on the efficacy of the reminder automatically, for example by consulting a look-up table. Furthermore, such a look-up table could be dynamically updated taking into account how effective reminders are.

In some embodiments, the user may pick from a large selection of possible activities. In other embodiments, the system may select appropriate activities without a user input, for example based on a prestored set of criteria.

Figure 3:
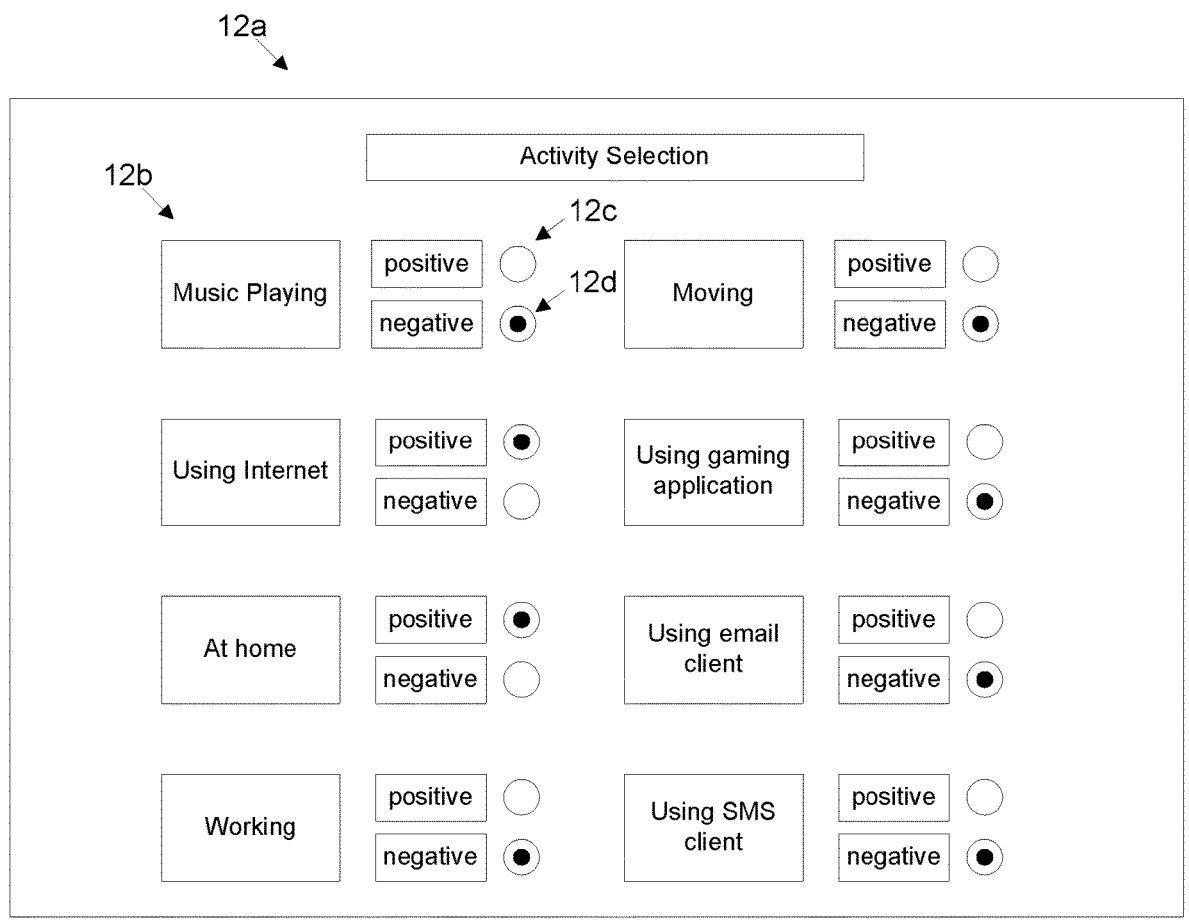
FIG. 3 shows a user interface for use in the first embodiment.

For example, the user could be presented with the activities shown in FIG. 3. FIG. 3 shows an example user interface 12a for enabling the user to indicate which of a set of activities are considered likely to have a positive or negative impact on the efficacy of the reminder. In this embodiment, the user interface 12a would be displayed on the display of the system 10.

As shown in FIG. 3, the interface 12a shows a number of activities 12b, along with check boxes 12c and 12d that the user can user to indicate if they consider that these activities have a positive or negative effect on the efficacy of the reminder for the task. In this embodiment, not ticking a check box for an activity indicates that the user considers that that activity has a neutral effect on the efficacy of the reminder.

If an activity is considered to have a positive effect on the efficacy of the reminder for the task, then the reminder is likely to be more efficacious if that activity is being carried out when a reminder alert is output. If the activity is considered to have a negative effect on the efficacy of the reminder for the task, then the reminder is likely to be less efficacious if that activity is being carried out when a reminder alert is output.

Each of these activities would be monitored by the monitor mechanism 13 in an appropriate way for each activity. The activities in FIG. 3 are:

Music Playing: This indicates whether the system 10 is playing music. In this example, the user has indicated that this has a negative impact on the efficacy of the reminder for the task. This may be because, for example, the user in general prefers to listen to music while not carrying out any administrative tasks (e.g. paying a bill), preferring instead to relax. This activity could be monitored by the monitor mechanism 13 by determining if a music function of the system 10 is activated.

Using Internet: This indicates whether the system 10 is accessing the Internet. In this example, the user has indicated that this has a positive impact on the efficacy of the reminder for the task. This may be because, for example, the user requires the use of the Internet to pay the utility bill. Hence, if the user is already using the Internet, a reminder to pay the utility bill may be more effective than if the user is engrossed in another activity. This activity could be monitored by the monitor mechanism 13 by determining if a web browser function of the system 10 is activated.

At home: This indicates whether the system 10 is at the designated home location of the user. In this example, the user has indicated that this has a positive impact on the efficacy of the reminder for the task. This may be because, for example, the user prefers to carry out administrative tasks such as paying bills while at home. This activity could be monitored by the monitor mechanism 13 by using a GPS function of the system 10, or another suitable location function.

Working: This indicates whether the user of system 10 is working, for example using a work related application on the system 10. In this example, the user has indicated that this has a negative impact on the efficacy of the reminder for the task. This may be because, for example, the user prefers to carry out administrative tasks while not working. This activity could be monitored by the monitor mechanism 13 by determining if the work related application on the system 10 is activated.

Moving: This indicates whether the system 10 is moving. In this example, the user has indicated that this has a negative impact on the efficacy of the reminder for the task. This may be because, for example, the user prefers to carry out administrative tasks while seated. This activity could be monitored by the monitor mechanism 13 by using an accelerometer function of the system 10.

Using gaming application: This indicates whether the user of system 10 is using a gaming application. In this example, the user has indicated that this has a negative impact on the efficacy of the reminder for the task. This may be because, for example, the user prefers not to be interrupted with playing games. This activity could be monitored by the monitor mechanism 13 by determining if a gaming application on the system 10 is activated.

Using email client: This indicates whether the user of system 10 is using an email client on the system 10. In this example, the user has indicated that this has a negative impact on the efficacy of the reminder for the task. This may be because, for example, the user prefers not to be interrupted with sending or reading emails. This activity could be monitored by the monitor mechanism 13 by determining if the email client on the system 10 is activated.

Using SMS client: This indicates whether the user of system 10 is using an SMS client on the system 10. In this example, the user has indicated that this has a negative impact on the efficacy of the reminder for the task. This may be because, for example, the user prefers not to be interrupted with sending or reading SMS messages. This activity could be monitored by the monitor mechanism 13 by determining if the email client on the system 10 is activated.

Furthermore, in this embodiment, there are other activities that have pre-stored influences on the efficacy of the reminder for the task, without requiring a user input. For example, the system 10 is arranged to store that making a telephone call using the system 10 has a negative impact on the efficacy of all reminders. Hence, for the activity of "making a call" it is not necessary to present the user with an option for choosing whether the activity has a positive or negative impact, as it is always considered to have a negative impact. Such activities could always be present in the activity information, regardless of whether the user is given a choice of which other activities comprise the activity information.

Hence, at step S2, the user's preferences for each selected activity, along with any activities whose influences on efficacy is predefined, are stored as activity information in the activity datastore 12.

At step S3, the monitor mechanism 13 monitors each of the selected activities, and at step S4 the user convenience index is calculated based on the monitoring. The user convenience index is calculated by considering the sum of the positive and negative influences on the efficacy of the reminder.

In this embodiment, an activity score is determined for each activity, with the user convenience index being a sum of the activity scores. In this embodiment, if an activity whose influence is positive is being performed, then an activity score of 1 is given. If an activity whose influence is negative is being performed, then an activity score of −1 is given. If the activity is not being performed (regardless of whether positive or negative), or if the user indicated that the activity had a neutral influence (e.g. by not ticking either the positive or negative check box in FIG. 3), then an activity score of 0 is given.

To help illustrate this example, three example states of the user will now be discussed with references to Table 1.

In state 1, the user is listening to music, using the internet, while walking in the park. The user is therefore not at home, and is moving. The user is not working, and not using a gaming application, email client or SMS client.

In state 2, the user is at home sitting down (and thus not moving), while making a call; while not using the internet, not listening to music, and not using a gaming application, email client or SMS client.

In state 3, the user is at home sitting down (and thus not moving), using the internet; while not listening to music, not working, and not using a gaming application, email client or SMS client.

The activity scores and user convenience index associated with states 1, 2 and 3 are shown in Table 1.

TABLE 1

| Activity | Score in State 1 | Score in State 2 | Score in State 3 |
|---|---|---|---|
| Music Playing | −1 | 0 | 0 |
| Using Internet | 1 | 0 | 1 |
| At home | 0 | 1 | 1 |
| Working | 0 | 0 | 0 |
| Moving | −1 | 0 | 0 |
| Using gaming application | 0 | 0 | 0 |
| Using email client | 0 | 0 | 0 |
| Using SMS client | 0 | 0 | 0 |
| Making a call | 0 | −1 | 0 |
| User convenience index | −1 | 1 | 2 |

At step S5, the reminder processor determines whether the user convenience index is greater than or equal to the stored threshold. In this example, the stored threshold is 2. Hence, for states 1 and 2, the user convenience index is determined to be less than the stored threshold. Therefore, for states 1 and 2, the system continues to monitor the user (step s3). [Again, please confirm that this example is sensible. I was making educated guesses]

For state 3, the user convenience index is determined to be equal to the stored threshold. Hence, the system progresses to step S6, and the reminder is output to the user to pay the utility bill.

Hence, in this embodiment, the user is presented with a reminder about a task at a time that is considered to be appropriate for that task. This is done by delivering the reminder when the user is carryout out (or not carrying out) certain activities that are considered to have a positive or negative effect on the efficacy of the reminder. This enables embodiments of the invention to provide much more effective reminders when compared to conventional systems that simply provide reminders at an absolute time. The reminder system according to this embodiment can be used to ensure that the reminder is delivered when the user is likely to be receptive to the reminder. Moreover, the user may establish a more positive association with the activity of which he/she is reminded because the reminder does not come at an inconvenient moment which may be perceived as annoying, but rather at a moment that he/she can act upon it.

In the above example, the reminder is not associated with a time period for carrying out the task. However, as discussed, in other embodiments, the task can be associated with a predetermined time window, e.g. "pay utility bill between the 15$^{th}$ and 17$^{th}$ of each month". This could be done by the user inputting the reminder using a suitable user interface on the device of the system 10, entering the text "Pay Utility Bill" and setting a date range as between the 15$^{th}$ the 17$^{th}$ of each month. In such embodiments, the output mechanism 15 would only output the reminder alert within the predetermined time window. This could be done by, for example, only monitoring the user (step S3) during the predetermined time window. This could also be done by monitoring the user at all times, but lowering the threshold to a very low value (so that the user convenience index is never greater than or equal to the threshold) during the predetermined time window. This could also be done by instructing the output mechanism 15 to only output the reminder alert within the predetermined time window, regardless of the value of the user convenience index. In some embodiments that use a predetermined time window for the reminders, the system 10 will ensure that the reminder is always output by the end of the predetermined time window. This could be done by outputting the reminder at the very end of the predetermined time window, regardless of the current activity of the user.

In some embodiments, the system 10 may determine that there are two time windows for different tasks with overlapping time windows. In such situations, in particular where the reminders may be related (e.g. both relating to taking a pill), the system 10 may consolidate the time windows.

In some embodiments, the reminder information may concern a task that is periodically repeated. In such embodiments, the time window for carrying out the task can be altered depending on when the task was last performed. For example, if a task is taking a medication that must be taken three times a day, it is generally advisable that the medication be taken as spaced apart as possible.

For example, an ideal set of time periods might be 7 am, 3 pm, 11 pm as these as equally spaced, which may correspond to preferred time windows of 6:30-7:30 am, 2:30-3:30 pm and 10:30 to 11:30 pm. However, if the user takes the first pill at 11 am, then the optimal time periods for taking the second and time pills would change. In such embodiments, the system 10 may be aware (e.g. by the setting of a user preference) that the user goes to bed at 11:30 pm, which fixes a boundary on when the third pill of the day could be taken. However, rather than reminding the user to take the second pill at 3 pm, the system may alter the time window for the second pill to be 5 to 6 pm. This enables an optimum spacing of such tasks.

In some embodiments, the reminder information can include information concerning a missed reminder cost associated with the task. The missed reminder represents the consequences of not acting on the reminder and allows alert procedures to be set and the threshold to be adjusted. For example, some tasks might be crucial and need to be performed within their time window. In such embodiments, the missed reminder cost may be a variable that increases as the time window for the reminder nears closing. For example, if the time window is 4 hours long, then the "cost" associated with the user ignoring the reminder early in the time window (e.g. within the first 5 minutes) is low, as there may well be other opportunities to remind the user within the time window (e.g. other times when the monitoring result is greater than or equal to the threshold). However, if the time window is nearly over, then the "cost" associated with the user ignoring the reminder is high, as there might be no opportune times to remind the user before the end of the time window. Hence, in such embodiments, the output mechanism 15 may determine the nature of the reminder alert to the user based on the missed reminder cost. For example, the missed reminder cost could be increase in a step-wise fashion with increasing time within the time window.

Furthermore, in some embodiments, the missed reminder cost could vary in other ways. An example being for medication that depends on certain measurements, e.g., diabetes medication that depends on blood sugar levels that vary. In such a case, the missed reminder costs may also vary with the variations in blood sugar levels for example.

In this embodiment the threshold for the monitoring result (e.g. user convenience index) is fixed. However, in other embodiments, the threshold may vary, either with time or as a result of another adjustment by the system 10. For example, in embodiments in which the reminder is associated with a predetermined time window, the threshold may be lowered towards the end of the predetermined time window, thus helping to ensure that the reminder is provided within the predetermined time window.

In other embodiments, the threshold may be varied by the system for other reasons. For example, as discussed in more detail below, the system 10 may monitor compliance with the reminder (i.e. whether the reminder was acted upon or ignored) and use this to vary the threshold.

In the above mentioned example, the possible activity scores for each activity are −1, 0 and 1, representing a simple positive, neutral (or activity not being performed) or negative effect on the efficacy of the reminder. However, in other embodiments, different activities can be associated with different weights, with the weights either being predetermined or set by the user. Hence, in such embodiments, when the user convenience index is calculated, it will take into account the differently weighted activity scores.

In this embodiment, when the user is presented with the reminder, the user can indicate that the task has been completed or dismiss the reminder. If the user dismisses the reminder, the system 10 will go back to monitoring the user, so as to issue further reminders at a later time, for example after a predetermined time delay. For example, the system 10 may wait 10 minutes and then start the monitoring process (step S3) again. The system 10 may use information on dismissed or ignored reminders to raise the threshold of the monitoring result and to learn which activity (the one that the user engaged in when he/she ignored the reminder) has a negative impact on the efficacy of the reminder and adapt the activity impact in the system (e.g. to the weights of the activity).

In some embodiments, the system 10 is arranged to determine if the task is performed following the output of the alert. For example, the system 10 may be able to monitor (e.g. using the monitor mechanism 13 or other monitoring equipment) that the task has been performed. For example, if the task is "go for a run", then the system 10 could use an accelerometer combined with a GPS sensor (or other suitable means) to determine if this has been performed following the reminder. The system 10 could also rely on a user input to determine if the task has been performed following the reminder.

In some embodiments, the system 10 may determine that the task for which the reminder is set has actually been performed before the reminder has been issued. In such scenarios, the system 10 may opt to not present the reminder to the user.

In embodiments in which the system 10 obtains information (either via a user input or by monitoring) that the task has been completed, the system 10 can store compliance information relating to the activities being performed by the user at the time of the task being completed as a compliance result. For example, the system 10 could analyze what activities (whether they are the ones stored in S2 or other activities monitored by the system 10) the user was carrying out while the task was performed, and use this information to improve the reminder system in an iterative way. For example, the system 10 could use the compliance result to adjust the weights of the activity scores, to add activities into the set of activities used to calculate the monitoring result (e.g. user convenience index), and/or to vary the threshold.

This is useful in many circumstances. For example, even though embodiments of the invention provide reminders that are more likely to be acted upon than conventional reminder systems, it is still possible that the reminder will be ignored. By using compliance result in this way, the system of such embodiments can adapt to the precise demands of the user in order to improve the efficiency of the reminder system.

Figure 4:
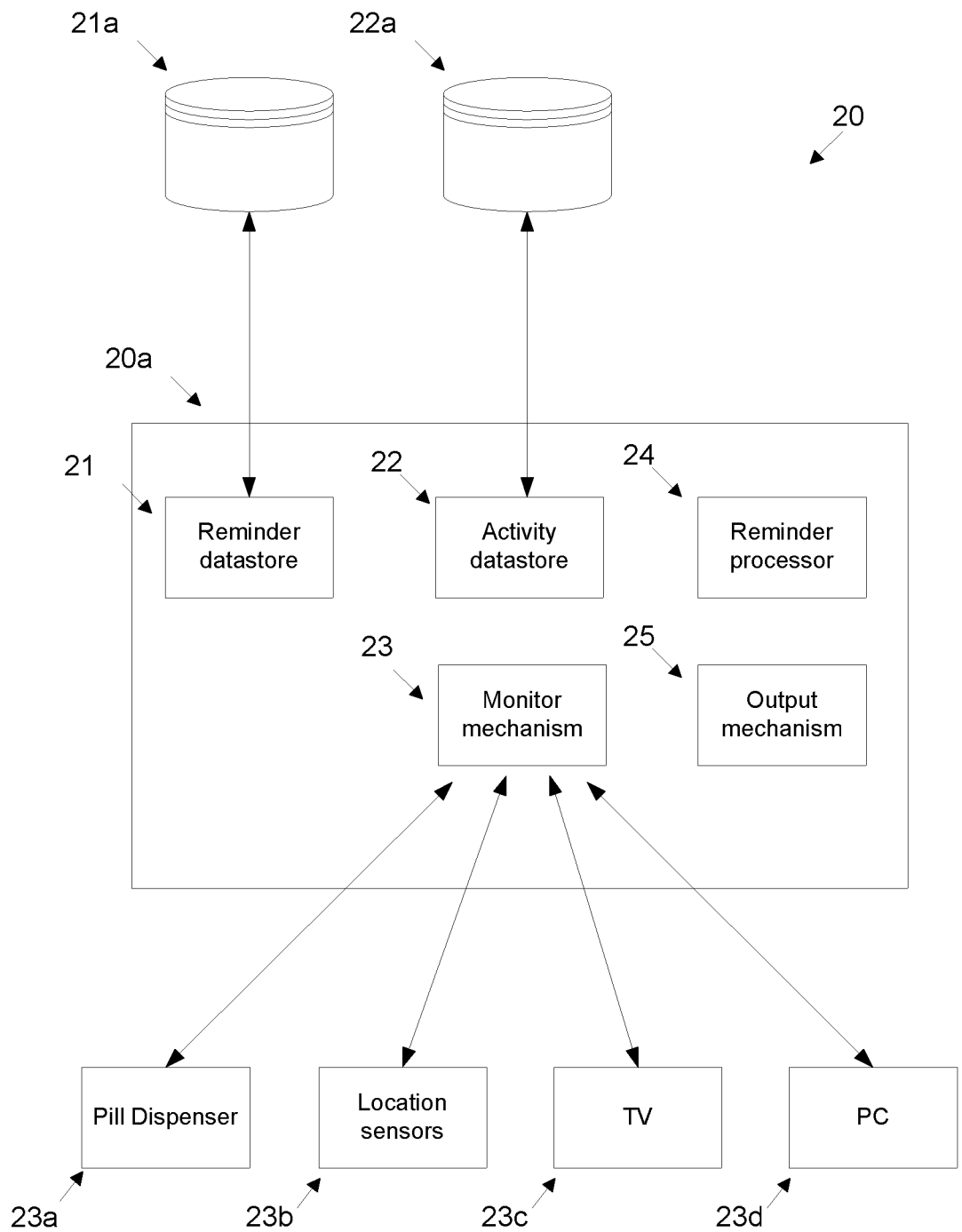
FIG. 4 schematically shows a system for monitoring a user according to a second embodiment of the invention.

FIG. 4 schematically shows a system 20 for monitoring a user according to a second embodiment of the invention. In this embodiment, the system 20 is specifically arranged to monitor the user's adherence to a medication regime. As a result, the user in the context of this embodiment is a patent with a long term health condition that requires a therapeutic regime into order to keep the user's long term health condition stable. In this example embodiment, it will be assumed that non-adherence with the user's therapeutic regime will lead to a worsening of the patient's symptoms. The system 20 is arranged to provide reminders to promote adherence to the therapeutic regime.

The system 20 comprises a device 20a and a number of remote devices, including a remote reminder database 21a, a remote activity database 22a and a number of remote monitor mechanisms 23a, 23b, 23c and 23d. The device 20a comprises a reminder database 21, an activity database 22, a monitor mechanism 23, a reminder processor 24 and an output mechanism 250.

The device 20a is in communication with the remote reminder database 21a, the remote activity database 22a and the remote monitor mechanisms 23a, 23b, 23c and 23d via suitable interfaces. For example, the device 20a could be connected to the remote reminder database 21a and the remote activity database 22a via a network, such as the internet. The device 20a could be connected to the remote monitor mechanisms 23a, 23b, 23c and 23d via a short range wireless connection, such as Bluetooth. It will, however, be appreciated that other embodiments could use other ways of connecting the remote devices to the device 20a.

In this embodiment, the device 20a is a portable device (e.g. a smart phone) carried by the user. In other embodiments, the device 20a could be a standalone device that is not portable. In other embodiments, the device 20a could be integrated into the functionality of a general purpose device.

In this embodiment, the remote monitor mechanisms are a pill dispenser 23a, location sensors 23b, a TV 23c and a personal computer (PC) 23d.

In this embodiment, the pill dispenser 23a is near field communication (NFC) enabled and can detect if the user is near the pill dispenser 23a, e.g. within a range of 1 m. In this embodiment, the user wears a suitable NFC device (e.g. a suitable bracelet), which is used by the pill dispenser 23a to detect if the user is within range. In other embodiments, the pill dispenser 23a could detect whether the user is within range by other means.

The pill dispenser 23a can also, in this embodiment, detect if a pill has been dispensed, and only dispense pills at the correct time. In this embodiment, the pill dispenser 23a can provide information on whether the user is near the pill dispenser 23a and whether a pill has been dispensed to the monitor mechanism 23. It will be assumed in the discussion below, for ease of explanation, that the pill dispenser 23a is in the user's kitchen.

In addition, in this embodiment, the pill dispenser 23a can also provide audible and visual alerts.

In this embodiment, the location sensors 23b are spaced apart in the user's house and can detect where in the house the user is, providing this information to the monitor mechanism 23.

In this embodiment, the TV 23c and the personal computer (PC) 23d can detect what actions the user is performing on them (e.g. whether a favored TV show is being watched on the TV 23c or whether the internet browser of the PC 23d is being use) and can provide this information to the monitor mechanism 23. It will be assumed in the discussion below, for ease of explanation, that the TV 23c and PC 23d are in the user's living room, where it is assumed that the user spends most of him time while at home.

In this embodiment, the output mechanism 25 is capable of providing an audible, vibrating and visual alert on the device 20a. The output mechanism 25 is also capable of instructing the pill dispenser 23a to provide an audible and visual alert. The output mechanism 25 can also interface with the TV 23c to enable the TV 23c to display a visual alert.

Figure 5:
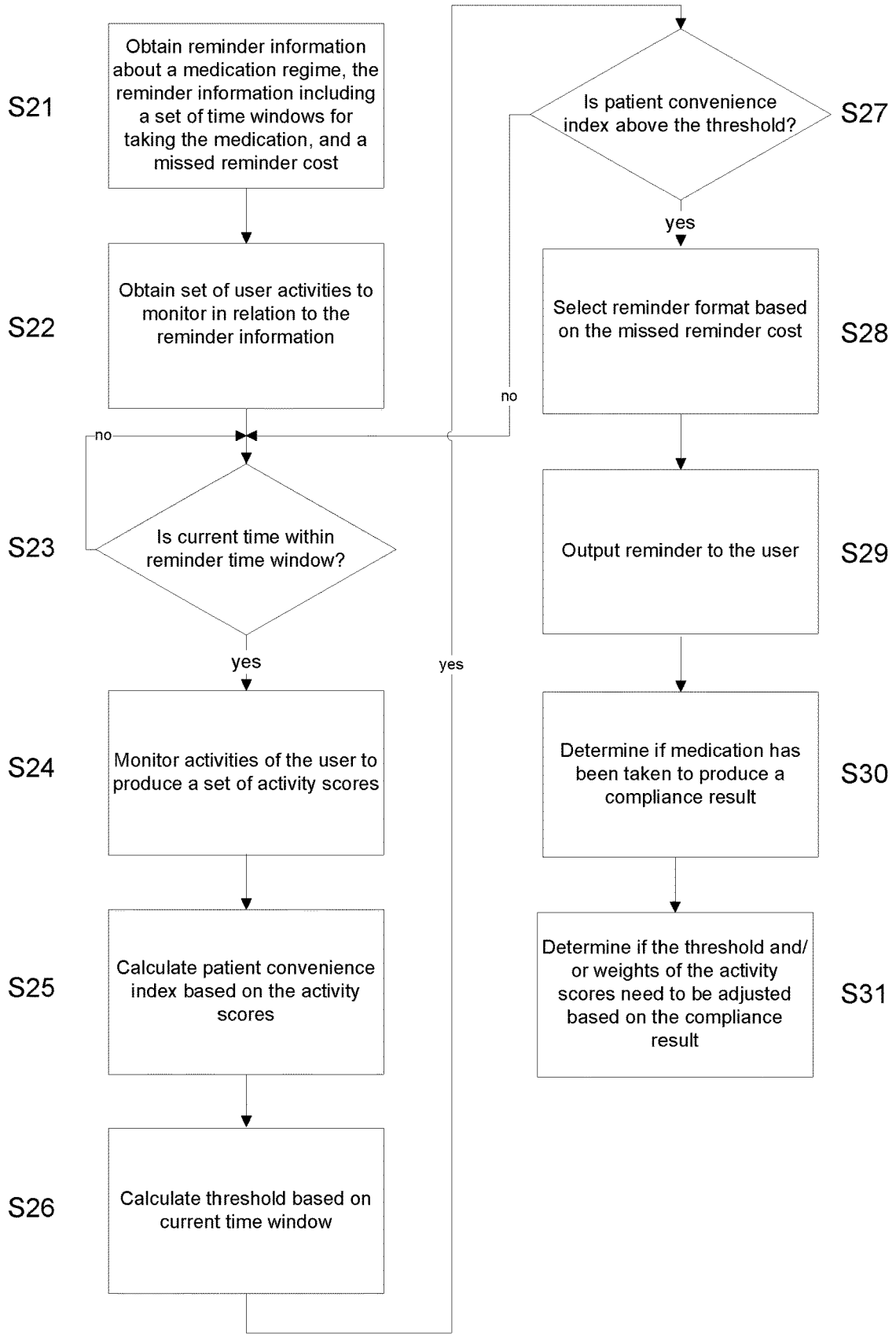
FIG. 5 shows a flow diagram explaining the operation of the system according to the second embodiment.

FIG. 5 shows a flow diagram explaining the operation of the system 20. This example shows how dynamically calculating the patient convenience index allows the system 20 to remind the patient to adhere to their therapeutic regime. For ease of explanation, it will be assumed that the therapeutic regime in this embodiment consists of a medication regime which requires the user to take a pill twice a day, with the intervals as spaced apart and as regular as possible. It will also be assumed the user in this embodiment is patient who is generally sedentary, spending much of his time watching television or using the internet.

At step S21, the system 20 obtains reminder information about a medication regime, the reminder information including a set of time windows for taking the medication, and a missed reminder cost. In this embodiment, this is done by the device 20a querying the remote reminder database 21a to obtain reminder information associated with the medication regime of the patient.

The information in the remote reminder database 21a could be obtained in a variety of different ways. For example it could be obtained by a health care professional uploading a care plan that includes data such as medication, exercise regime, and diet plan that the patient needs to adhere to. The reminder information could contain reminders for tasks associated with all aspects of this care plan. In other embodiments, a health care professional could scan a bar code relating to a medication (or enter a suitable reference number), which would load information on the medication including the schedule for taking it. In other embodiments, the details could be obtained by the remote reminder database 21a in other ways, for example by manual input.

In this embodiment the reminder information includes time windows for which the medication should be taken, as the task of taking the pill must be taken twice a day.

At step S22, the system 20 obtains information on a set of user activities used to monitor the user and stores this as activity information. In this embodiment, this is done by the device 20a querying the remote activity database 22a to obtain details of which activities are the most important to efficacy of the tasks included in the reminder information. The activity information could also take into account the capabilities of the system 20, e.g. relating to which activities the system 20 is capable of monitoring.

In this embodiment, the monitor mechanism 23 is connected to remote monitor mechanisms that include the NFC enabled pill dispenser 23a, location sensors 23b, the TV 23c and the personal computer (PC) 23d, which are relevant to the task (taking a pill) in this embodiment. Hence, the activity information contains the activities associated with these remote monitors, along with whether these activities have a weighted positive or negative likely effect on the efficacy of a reminder for the task (taking the pill).

In this embodiment, the monitor mechanism 23 is further able to determine if the user is making a telephone call, and this activity is included in the activity information.

Once the system 20 has obtained the reminder information and the activity information, the system 20 can begin monitoring the user. In this embodiment, the task included in the reminder information is associated with reminder time windows. In the example of a pill that must be taken twice a day, the reminder time windows may take into account the sleeping habits of the user so as to determine two time periods in the day that serve to equally space out the medication. For example, for a user who wakes at 7 am and goes to bed at 11 pm, the reminder time windows might be 7:30-9:30 am and 7:30-9:30 pm.

In some embodiments, the reminder time windows could be included in the reminder information and provided to the system 20, or could be determined by the system 20 from information in the reminder information (e.g. taking into account known behavior patterns of the user). In other embodiments, the reminder time windows could be user defined or a combination of any of the above.

At step S23, the system 20 determines whether the current time is within a reminder time window.

In this embodiment, if the current time is within a reminder time window, the monitor mechanism 23 begins monitoring the user (step S24). If the current time is not within a reminder time window, then the system waits until it is.

In step S24, the monitor mechanism 23 monitors each of the activities included in the activity information. In this embodiment, the monitor mechanism 23 receives data from the remote monitor mechanisms 23a, 23b, 23c and 23d as well data on other activities such as whether the user making a telephone call. The monitor mechanism 23 assigns an activity score to the activities being monitored, depending on whether the activities are being performed or not. As discussed in more detail below, the activity scores are weighted in accordance with their likely effect on the efficacy of the reminder to take the pill.

At step S25, the system 20 calculates a patient convenience index by summing the activity scores. At step S26, the system 20 calculates a current threshold based on the current time within the active time window. In this embodiment, as will be discussed below, the threshold can vary according to the time within the active time window, and on compliance information that indicates how successful previous reminders have been.

At step S27, the reminder processor 24 determines whether the patient convenience index is above the threshold.

Steps S24 to S27 will be explained with reference to Table 2, which shows the activities in the activity information in this embodiment, along with their weights. Also included are four example activity scores for four states of the user.

TABLE 2

| Activity | Weights | Score in State 1 | Score in State 2 | Score in State 3 | Score in State 4 |
|---|---|---|---|---|---|
| Watching a ppv film | −3 | −3 | 0 | 0 | 0 |
| Watching a preferred TV show | −2 | 0 | −2 | 0 | 0 |
| Watching other TV | −1 | 0 | 0 | −1 | 0 |
| Using the Internet | −1 | −1 | 0 | 0 | 0 |
| Moving around the house | −1 | 0 | −1 | 0 | 0 |
| In kitchen | +2 | 0 | +2 | +2 | +2 |
| Near Pill dispenser | +4 | 0 | 0 | +4 | +4 |
| Making a telephone call | −10 | 0 | 0 | 0 | −10 |
| User convenience index | | −4 | −1 | +5 | −4 |

In this embodiment, as discussed, the TV 23c can monitor what is being displayed on it and provide this information to the monitor mechanism 23. In this embodiment, the TV 23c can monitor whether the user is watching a pay per view (ppv) film, watching a preferred TV show, or watching other TV (i.e. not a ppv film or preferred show).

In this embodiment, it is considered likely that the user watching TV will have a negative impact on the efficacy of the reminder to take the pill, with watching a ppv film (where it is assumed that the user, having paid for the content, is particularly engrossed) having the most negative impact, as so being assigned a weight of −3. Watching a preferred TV show is assigned a weight of −2, and watching other TV is assigned a weight of −1.

In this embodiment, as discussed, the PC 23s can monitor what is being used on the PC, and provide this information to the monitor mechanism 23. In this embodiment, it is considered likely that the user using the internet will have a negative impact on the efficacy of the reminder to take the pill. Hence, using the internet is assigned a weight of −1.

The location sensors 23b can detect that the user is moving around the house (e.g. by detecting movement from one room to another within a time period). In this embodiment, it is considered likely that the user moving around will have a negative impact on the efficacy of the reminder to take the pill. This is because the user in this embodiment is generally sedentary, and thus movement around the house is likely to have specific purpose (e.g. going to the bathroom). Hence, moving around the house is assigned a weight of −1.

The location sensors 23b can detect that the user is in their kitchen. As the pill dispenser 23a is in the user's kitchen, it is considered likely that the user being in the kitchen will have a strong positive impact on the efficacy of the reminder to take the pill. Hence, being in the kitchen is assigned a weight of +2.

The NFC enabled pill dispenser 23a can detect that the user is proximate it. Being proximate the pill dispenser 23a is to have a very strong positive impact on the efficacy of the reminder to take the pill. Hence, being near the pill dispenser 23a is assigned a weight of +4.

The monitor mechanism 23 can detect that the user is making a phone call. It is considered that a reminder while the user is making a phone call is very unlikely to be effective. Hence, making a telephone call is assigned a weight of −10.

The patient convenience index is the sum of the weighted activity scores in this embodiment.

$$PCI = \sum_{activities} weight \times score$$

Four states of the user are shown in Table 2. In state 1, the user is watching a ppv film and using the internet, while sitting down. The user is therefore not likely to want to be distracted by a reminder to take a pill. Hence, the patient convenience index is low (−4), indicating that a reminder at this time is unlikely to be effective.

In state 2, the user the user is watching a preferred TV show, while moving around the house and in the kitchen. It can be inferred that because a preferred TV show is being played on TV and that the user has moved to the kitchen that the user is just getting something (e.g. a drink) before going to the preferred TV show. Hence, the patient convenience index, while higher than state 1, is low (−1), indicating that a reminder at this time is not very likely to be effective.

In state 3, the user is watching another other (non-preferred) TV show, while in the kitchen and near the pill dispenser 23a and not moving around. It can be inferred that because the user has been in the kitchen for some time (as not moving) and that a non-preferred TV show is being played on TV that the user is in the kitchen to make or eat food. The user is also physically near the pill dispenser 23a (e.g. within 1 m). The user is therefore very likely to be susceptible to a reminder in this state, and hence the patient convenience index is high (+5) indicating that a reminder at this time is likely to be effective.

In state 4, the user is in the kitchen and near the pill dispenser 23a and not moving around. The use is also taking a phone call. While being in the kitchen, being near the pill dispenser 23a, and not moving around factors have a strong positive effect on the efficacy of the reminder to take the pill, the fact that the user is making a telephone call has a strong negative effect of the efficacy of the reminder. Hence, the patient convenience index is low (−4) indicating that a reminder at this time is not likely to be effective.

At step S27, the reminder processor 24 determines whether the user convenience index is greater than or equal to the threshold. In this embodiment, the threshold varies with time within the time window. For example, if the time window is 7:30-9:30 pm, then the threshold may be lower for the first half and hour that for the last half and hour of this window. For example, the threshold may vary according to Table 3.

TABLE 3

| Time within window | Threshold |
|---|---|
| 7:30-8:00 pm | +5 |
| 8:00-9:00 pm | 0 |
| 9:00-9:30 pm | −1 |

Hence, in this example, within the first part of the time window (7:30-8:00 pm), a reminder will only be output if the patient convenience index is greater than or equal to +5. Hence, if the user is in state 3, the reminder would be output. In the second part of the time window (8:00-9:00 pm), the threshold is lowered, and in the final part of the time window (9:00-9:30 pm), the threshold is lowered still.

In some embodiments, the reminder alert will be issued at the end of the time window, regardless of the current patient convenience index. This can correspond to setting a threshold so low that all possible patient convenience indexes will be greater than the threshold. In such a case, the threshold may vary according to Table 4.

TABLE 4

| Time within window | Threshold |
|---|---|
| 7:30-8:00 pm | +5 |
| 8:00-9:00 pm | 0 |
| 9:00-9:30 pm | −1 |
| 9:30 pm onwards | −100 |

As discussed, if the patient convenience index is greater than or equal to the threshold, then the process moves to step S28. If the patient convenience index is not greater than or equal to the threshold, then the process moves to back to step S23.

At step S28, the system 20 selects a reminder format, with is output at step S29. As discussed, in this embodiment, the output mechanism 25 is capable of providing an audible, vibrating and visual alert, and the format of the reminder (e.g. purely audible, volume, or combination of audible and vibrating) can vary according to the cost of the missed reminder.

In this embodiment, when the user is presented with the reminder, the user can indicate that the task has been completed or dismiss the reminder. If the user dismisses the reminder, the system 20 will go back to step S23, so as to issue further reminders at a later time, for example after a predetermined time delay. For example, the system 20 may wait 10 minutes and then start the process of step S23 again. In some embodiments, the system 20 may continue providing the alert until the user either satisfies the reminder (e.g. takes the pill) or dismisses the reminder.

It will be appreciated that even though this embodiment provides improved reminders when compared to conventional systems, the user can still ignore or dismiss the reminder. If the current time is early within the time window, then the cost of a dismissed or ignored reminder is lower than later in the time window. This can be used to increase the likelihood of the reminder not being ignored later in the time window, by making the reminder alert more intrusive (e.g. louder, vibrating).

For example, if the time window is 7:30-9:30 pm, then the reminder alerts may have the formats shown in Table 5:

TABLE 5

| Time within window | Format of reminder alert |
|---|---|
| 7:30-8:00 pm | Audible alert on device at normal volume, visual alert on the device and the pill dispenser |
| 8:00-9:00 pm | Audible alert on device at higher volume, audible alert on the pill dispenser, visual alert on the device and the pill dispenser |
| 9:00-9:30 pm | Audible at highest volume on device, audible alert on the pill dispenser, vibrating alert on the device, visual alert on TV |

Hence, early in the time window (7:30-8:00 pm), the format of the reminder alert may be an audible alert on device 20a at normal volume, along with a visual alert on both the device 20a and the pill dispenser 23a.

In the middle section (8:00-9:00 pm), the format of the reminder alert may be an audible alert on device 20a at higher volume, an audible alert on the pill dispenser 23a, along with a visual alert on both the device 20a and the pill dispenser 23a.

In the last section (9:00-9:30 pm), the format of the reminder alert may be an audible alert on the device 20a at the highest volume, an audible alert on the pill dispenser 23a, visual alerts on both the device 20a and the pill dispenser 23a, a vibrating alert on the device 20a, along with a visual alert on the TV 23c (as the system 20 may provide such information to the TV 23c).

In some embodiments, if the user engages in the to-be-reminded behavior outside of the time window and not in the time window, then the system can adaptively shift the time window to include that moment that the user performed the behavior because this apparently was an opportune moment for him/her.

At step S30, the system 20 determines if the pill has been taken to produce a compliance result. This is done by using the pill dispenser 23, which will detect whether the user receives a pill from it. The system 20 then determines a compliance result. At step S31, the system 20 determine if the threshold and/or weights of the activity scores need to be adjusted based on the compliance result.

In more detail, at step S30, the system 20 analyze what activities capable of being monitored by the system 20 were being carried out when the user was reminded about the taking the pill, if the reminder was issued shortly before (e.g. within 2 minutes) the pill was taken. Alternatively, or in addition, the system 20 analyze what activities were being carried out when the pill dispenser 23c dispensed the pill. The system 20 can then use this information to adjust the weights of the activity scores. For example, if it is found that that a reminder is repeatedly effective even when an activity that was previously considered to have a negative effect is being carried out (e.g. low weight), then it may be the case that the weight of that activity should be increased. Furthermore, if it is found that that a reminder is repeatedly ineffective when an activity that was previously considered to have a positive effect is being carried out (e.g. high weight), then it may be the case that the weight of that activity should be decreased.

In a similar way, information on activities being performed just prior to a successful (or unsuccessful) reminder could be used to adjust the threshold either up or down.

Furthermore, if it is found that the user spontaneously takes a pill in the reminder time window, without a reminder (e.g. because at the current time it was considered by the sums of the activity scores that the user was not susceptible to a reminder), then it may be the case that the user was actually more susceptible than previously thought. This information could be used to adjust the threshold or adjust the individual weights of the activities being carried out at the time.

In this embodiment, the user is provided with reminder alerts about a task related to their therapeutic regime at times that are considered to be appropriate for that task. This is done by delivering the reminders when the user is carryout out (or not carrying out) certain activities that are considered to have a positive or negative effect on the efficacy of the reminder. Hence, such embodiments provide important benefits in ensuring that the user maintains their therapeutic regime.

Embodiments of the invention are suitable for reminders any tasks that form part of a therapeutic regime, e.g. medication, exercise or any other task or activity recommended as part of the regime.

As a further example, consider an employee who is a bit overworked and his doctor has prescribed to take some moments of relaxation throughout the day. In this case the therapeutic regime comprises a treatment plan that simply includes the need to relax. Many individuals in such a situation may tend to forget about such a treatment plan in the flow of the normal workday. Embodiments of the invention (such as what is shown in FIG. 4) can help trigger the employee to relax at opportune moments, that his daily schedule allows for relaxation and trigger him to go for a walk or take a moment for meditation depending on his schedule and current activities.

For example, the employee could wear an activity sensor which measures his physical activity, with this activity sensor acting as a remote monitor mechanism in communication with a monitor mechanism in his tablet device. His tablet device could act as a central device in the system, and could store his calendar with his work appointments. The monitor mechanism in his tablet device could query his calendar to see when he is in a meeting (and therefore should not be bothered with reminders for relaxation). He could also wear a bracelet that measures his arousal levels, with this bracelet acting as a remote monitor mechanism in communication with a monitor mechanism in his tablet device.

In this case, a user convenience index could be calculated based on his calendar. Moments where there are no meetings could be considered convenient (e.g. +1) and moments that there are meetings are inconvenient (e.g. −1). The actual moment of finalizing the meeting can be measured based on a peak in physical activity from getting up from the chair and walking away from the meeting room to the desk (using the activity sensor). This could create a peak in the user convenience index (e.g. +4) since this is an opportune moment to trigger him for a relaxation moment (e.g., go for a walk or do a breathing exercise) after the meeting and right before he is starting a new activity (not a meeting but potentially some task behind his desk).

When the activity stops and he sits down behind his desk again the user convenience index drops to +1 again, when a new meeting starts it drops to −1.

The longer the employee has not taken a moment to relax, the missed reminder cost could be set rise. Also based on the measured arousal, the missed reminder cost will rise when arousal levels are high for too long (due to stressful activities). In this example the missed reminder costs may vary with his stress levels, being higher when he is stressful for some time, and being lower when is in a relaxed state for some time (so regardless of predetermined windows).

As discussed above, embodiments of the invention provide a system (either a single or distributed device) for providing a reminder to a user is provided that stores reminder information relating to a task that the user wishes to be reminded about, along with activity information comprising information on activities that are considered to have an effect on the efficacy of the reminder associated with the task. The system monitors the user to determine if the activities in the activity information are being performed to produce a monitoring result, and then determines when to remind the user about the task based on the monitoring result by comparing the monitoring result to a stored parameter (e.g. a threshold). A reminder alert is then output to the user on the basis of the comparison of the monitoring result and the stored parameter (for example when the monitoring result meets or exceeds the threshold). It will be appreciated that the stored parameter may be a dynamic quantity that is transiently stored.

While some embodiments use a threshold as the stored parameter, other embodiments could use other parameters for the comparison. For example, the output of the monitor mechanism (i.e. the monitoring result) could be a code (e.g. converted from weighted activity scores into a code) that is compared to a stored code. When the monitoring result code matches the stored code, then the reminder could be output.

In some embodiments, the system can further comprises a user preference datastore arranged to store information on one or more reminder preferences of the user, and the reminder processor could be arranged to determine when to remind the user about the task taking into account the or each reminder preference of the user. For example, the threshold could be lowered or raised based on certain times of the day that the user has indicated have either a negative or positivity effect on the efficacy of the reminder associated with the task. By measuring activities of the user, it is possible to gauge information on the user's likely emotional or cognitive state. For example, if the user's sleep is measured, and it is found that that user's sleep activity is lower than normal (or lower than a set level), then the system could determine that the user may be tired, and hence output (or not output) reminders appropriately.

It will be appreciated that the hardware used by embodiments of the invention can take a number of different forms. For example, all the components of the system could be provided by a single device (e.g. the example of FIG. 1), or different components of the system could be provided on separate devices. An examples of such an arrangement is the system of FIG. 4, in which a number of the components of the respective systems are provided on a device, whereas other components are provided on remote devices (with "remote" in this context meaning not part of the device, but communicable with the device). More generally, it will be appreciated that embodiments of the invention can provide a system that comprises one device or several devices in communication.

It will be appreciated that the term "comprising" does not exclude other elements or steps and that the indefinite article "a" or "an" does not exclude a plurality. A single processor may fulfill the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalization thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A system for providing a reminder to a user, the system comprising:
   a reminder datastore configured to store reminder information relating to a task that the user wishes to be reminded about;
   an activity datastore configured to store activity information comprising information on activities that are considered to have an effect on efficacy of the reminder associated with the task;
   a monitor mechanism configured to:
      monitor the user to determine whether the user is performing one or more activities on the system for which activity information is stored in the activity datastore, wherein the one or more activities comprise at least one of playing music on the system, using the Internet on the system, using a gaming application on the system, and using an SMS client on the system,
monitor each activity of the one or more activities on the system that corresponds to the stored activity information,
assign an activity score to each activity based on whether that activity is being performed,
assign different weights to each activity score, wherein each weighted activity score reflects a respective impact on the efficacy of the reminder, and
produce a monitoring result based on the determination, wherein the monitoring result is a sum of the weighted activity scores;
a reminder processor configured to:
determine when to remind the user about the task based on the monitoring result,
compare the monitoring result to a user convenience index threshold,
determine whether the task is performed following the output of the reminder alert,
use the sum of the activities scores to determine a compliance result, and
adjust the user convenience index threshold based upon the compliance result;
an output mechanism configured to output a reminder alert to the user after the monitoring result meets or exceeds the user convenience index threshold and the user is within range of a Near Field Communication (NFC) device.

2. The system according to claim 1, wherein the system is configured to use the compliance result to adjust the weight values of the weighted activity scores.

3. The system according to claim 1, wherein the reminder information includes information concerning a time window associated with the task, and the output mechanism is further configured to only output reminders within the time window.

4. The system according to claim 3, wherein the reminder information relates to a task that is periodically repeated and the time window is determined on the basis of when the task was last performed.

5. The system according to claim 3, wherein the user convenience index threshold is configured to vary with time and lower with increasing time within the time window.

6. The system according to claim 3, wherein the output mechanism is further configured to output the reminder alert to the user at the end of the time window, regardless of the monitoring result.

7. The system according to claim 3, wherein the reminder information includes information concerning a missed reminder cost related to a consequence of the reminder alert not being performed in the time window.

8. The system according to claim 7, wherein the output mechanism is further configured to determine the nature of the reminder alert to the user based on the missed reminder cost.

9. The system according to claim 7, wherein the system is configured to adjust the user convenience index threshold based on the missed reminder cost.

10. The system according to claim 7, wherein the system is configured to adjust the weight values of the weighted activity scores based on the missed reminder cost.

11. The system according to claim 1, wherein the task relates to an aspect of the user's therapeutic regime.

12. The system according to claim 1, wherein the activities for which activity information is stored in the activity information include actions of the user or passive activities such as where the user is located.

13. The system according to claim 1, wherein the system further comprises:
a user preference datastore configured to store information on reminder preferences of the user, wherein the reminder processor is further configured to determine when to remind the user about the task taking into account each reminder preference of the user.

14. A method of providing a reminder to a user, the method comprising:
storing reminder information relating to a task that the user wishes to be reminded about;
storing activity information comprising information on activities that are considered to have an effect on efficacy of the reminder associated with the task;
monitoring the user to determine whether the user is performing one or more activities on the system for which activity information is stored in an activity datastore;
monitoring each activity of the one or more activities on the system that corresponds to the stored activity information, wherein the one or more activities comprise at least one of playing music on the system, using the Internet on the system, using a gaming application on the system, and using an SMS client on the system;
producing a monitoring result based on the determination;
determining when to remind the user about the task based on the monitoring result and comparing the monitoring result to a user convenience index threshold;
outputting a reminder alert to the user on the basis of the comparison of the monitoring result and the user convenience index threshold;
outputting the reminder alert to the user when the monitoring result meets or exceeds the user convenience index threshold and the user is within range of a Near Field Communication (NFC) device;
assigning an activity score to each activity based on whether that activity is being performed;
assign different weights to each activity score, wherein each weighted activity score reflects a respective impact on the efficacy of the reminder,
monitoring each activity in the activity information, wherein the monitoring result is a sum of the weighted activity scores;
determining whether the task is performed following the output of the reminder alert;
using the sum of the activities scores to determine a compliance result; and
using the compliance result to adjust the threshold.

* * * * *